United States Patent
Dale et al.

(10) Patent No.: US 9,814,754 B2
(45) Date of Patent: Nov. 14, 2017

(54) COMBINATIONS WITH A BACKBONE-CYCLIZED PEPTIDE

(71) Applicant: POLYPHOR AG, Allschwil (CH)

(72) Inventors: Glenn E. Dale, Basel (CH); Daniel Obrecht, Bättwil (CH); Francesca Bernardini, Hésingue (FR)

(73) Assignee: Polyphor AG, Allschwil (CH)

( * ) Notice: Subject to any disclaimer, the term of this patent is extended or adjusted under 35 U.S.C. 154(b) by 0 days.

(21) Appl. No.: 14/419,992

(22) PCT Filed: Aug. 7, 2013

(86) PCT No.: PCT/EP2013/066551
§ 371 (c)(1),
(2) Date: Feb. 6, 2015

(87) PCT Pub. No.: WO2014/023766
PCT Pub. Date: Feb. 13, 2014

(65) Prior Publication Data
US 2015/0224168 A1    Aug. 13, 2015

(30) Foreign Application Priority Data

Aug. 8, 2012  (EP) .................... 12005743

(51) Int. Cl.
| | |
|---|---|
| *A61K 38/12* | (2006.01) |
| *C07K 5/12* | (2006.01) |
| *C07K 7/64* | (2006.01) |
| *A61K 45/06* | (2006.01) |
| *A61K 31/405* | (2006.01) |
| *A61K 31/496* | (2006.01) |
| *A61K 31/7036* | (2006.01) |
| *A61K 31/7052* | (2006.01) |
| *A61K 31/407* | (2006.01) |
| *A61K 47/48* | (2006.01) |
| *A61K 38/00* | (2006.01) |

(52) U.S. Cl.
CPC ............ *A61K 38/12* (2013.01); *A61K 31/405* (2013.01); *A61K 31/407* (2013.01); *A61K 31/496* (2013.01); *A61K 31/7036* (2013.01); *A61K 31/7052* (2013.01); *A61K 45/06* (2013.01); *C07K 5/12* (2013.01); *C07K 7/64* (2013.01); *A61K 38/00* (2013.01); *A61K 47/48407* (2013.01)

(58) Field of Classification Search
None
See application file for complete search history.

(56) References Cited

FOREIGN PATENT DOCUMENTS

| WO | WO2007079605 A2 * | 7/2007 | ............... C07K 7/06 |
|---|---|---|---|
| WO | WO 2010/017273 A2 | 2/2010 | |

OTHER PUBLICATIONS

Baldwin et al. Meropenem. A Review of its Use in the Treatment of Serious Bacterial Infections. Drugs 2008; 68 (6): 803-838.*
Bonfiglio et al. Recent developments in carbapenems. Expert Opin. Investig. Drugs (2002) 11(4):529-544.*

* cited by examiner

*Primary Examiner* — Satyanarayana R Gudibande
*Assistant Examiner* — Jia-Hai Lee
(74) *Attorney, Agent, or Firm* — Birch, Stewart, Kolasch & Birch, LLP

(57) ABSTRACT

A novel combination comprising a β-hairpin peptidomimetic of the formula cyclo(-Thr-Trp-Ile-Dab-Orn-$^D$Dab-Dab-Trp-Dab-Dab-Ala-Ser-$^D$Pro-Pro) (I), and a further compound with antibiotic activity, that enable therapeutic control of specific bacterial infections in human or animals at doses of the individual compounds lower than either of the compounds administered alone. The combination can be used as a medicament to treat e.g. skin or soft tissue infections; eye, ear, blood stream, or intra-abdominal infections; infections related to respiratory diseases, to bone diseases, to cardiovascular diseases, to genitourinary diseases, or to gastrointestinal diseases.

24 Claims, No Drawings

COMBINATIONS WITH A BACKBONE-CYCLIZED PEPTIDE

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "24657_ST25.txt" created on Dec. 1, 2015 and is 889 bytes in size. The sequence listing contained in this .txt file is part of the specification and is herein incorporated by reference in its entirety.

The present invention provides a combination of compounds that enable therapeutic control of specific bacterial infections in human or animals at doses of the individual compounds lower than either of the compounds administered alone. One of the compounds is a pathogen-specific antibiotic backbone-cyclized peptide incorporating a chain of 12 α-amino acid residues attached to a template which provides specific structural constraints for a β-hairpin-like conformation showing high efficacy and bio-availability, and remarkably long half-life in vivo.

The growing problem of microbial resistance to established antibiotics has stimulated intense interest in developing novel antimicrobial agents with new modes of action (H. Breithaupt, *Nat. Biotechnol.* 1999, 17, 1165-1169). One emerging class of antibiotics is based on naturally occurring cationic peptides (T. Ganz, R. I. Lehrer, *Mol. Medicine Today* 1999, 5, 292-297; R. M. Epand, H. J. Vogel, *Biochim. Biophys. Acta* 1999, 1462, 11-28). These include disulfide-bridged β-hairpin and β-sheet peptides (such as the protegrins [O. V. Shamova, H. A. Korneva, R. I. Lehrer, *FEBS Lett.* 1993, 327, 231-236], tachyplesins [T. Nakamura, H. Furunaka, T. Miyata, F. Tokunaga, T. Muta, S. Iwanaga, M. Niwa, T. Takao, Y. Shimonishi, Y. *J. Biol. Chem.* 1988, 263, 16709-16713], and the defensins [R. I. Lehrer, A. K. Lichtenstein, T. Ganz, *Annu. Rev. Immunol.* 1993, 11, 105-128], amphipathic α-helical peptides (e.g. cecropins, dermaseptins, magainins, and mellitins [A. Tossi, L. Sandri, A. Giangaspero, *Biopolymers* 2000, 55, 4-30]), as well as other linear and loop-structured peptides. Although the mechanisms of action of antimicrobial cationic peptides are not yet fully understood, their primary site of interaction is the microbial cell membrane (H. W. Huang, *Biochemistry* 2000, 39, 8347-8352). Upon exposure to these agents, the cell membrane undergoes permeabilization, which is followed by rapid cell death. However, more complex mechanisms of action, for example, involving receptor-mediated signaling, cannot be ruled out (M. Wu, E. Maier, R. Benz, R. E. Hancock, *Biochemistry* 1999, 38, 7235-7242; M. Scocchi, A. Tossi, R. Gennaro, *Cell. Mol. Sci.* 2011, 68, 2317-2330).

The antimicrobial activities of many of these cationic peptides usually correlate with their preferred secondary structures, observed either in aqueous solution or in membrane-like environments (N. Sitaram, R. Nagaraj, *Biochim. Biophys. Acta* 1999, 1462, 29-54). Structural studies by nuclear magnetic resonance (NMR) spectroscopy have shown that cationic peptides such as protegrin 1 (A. Aumelas, M. Mangoni, C. Roumestand, L. Chiche, E. Despaux, G. Grassy, B. Calas, A. Chavanieu, A. *Eur. J. Biochem.* 1996, 237, 575-583; R. L. Fahrner, T. Dieckmann, S. S. L. Harwig, R. I. Lehrer, D. Eisenberg, J. Feigon, *J. Chem. Biol.* 1996, 3, 543-550) and tachyplesin I (K. Kawano, T. Yoneya, T. Miyata, K. Yoshikawa, F. Tokunaga, Y. Terada, S. J. Iwanaga, S. *J. Biol. Chem.* 1990, 265, 15365-15367) adopt well defined β-hairpin conformations, due to the constraining effect of two disulfide bridges. However, the high hemolytic activity hindered their widespread use as antibiotics. Recent structural studies by NMR have indicated that the high hemolytic activity apparently correlates with the highly amphipathic nature of this cyclic β-hairpin-like molecule, but that it is possible to dissociate antimicrobial and hemolytic activities by modulating the conformation and amphiphilicity (L. H. Kondejewski, M. Jelokhani-Niaraki, S. W. Farmer, B. Lix, M. Kay, B. D. Sykes, R. E. Hancock, R. S. Hodges, *J. Biol. Chem.* 1999, 274, 13181-13192; C. McInnes L. H. Kondejewski, R. S. Hodges, B. D. Sykes, *J. Biol. Chem.* 2000, 275, 14287-14294).

Recently a series of antibiotic compounds following these design criteria are disclosed in WO2007079605, respectively WO2007079597, which combine a high efficacy specifically against *Pseudomonas aeruginosa* with low hemotoxic effects. This series is following earlier disclosures introducing these concepts in WO2002070547 and WO2004018503. With the compounds described therein, a new strategy was introduced to stabilize β-hairpin conformations in backbone-cyclic cationic peptide mimetics exhibiting high selective antimicrobial activity. This involved transplanting the cationic and hydrophobic hairpin sequence onto a template, whose function is to restrain the peptide loop backbone into a hairpin geometry.

Template-bound hairpin mimetic peptides of this type have been also described in the literature (D. Obrecht, M. Altorfer, J. A. Robinson, *Adv. Med. Chem.* 1999, 4, 1-68; J. A. Robinson, *Syn. Lett.* 2000, 4, 429-441) and the ability to generate β-hairpin peptidomimetics using combinatorial and parallel synthesis methods has been established (L. Jiang, K. Moehle, B. Dhanapal, D. Obrecht, J. A. Robinson, *Helv. Chim. Acta.* 2000, 83, 3097-3112).

An alternative approach to counteract the increasing prevalence and spread of multidrug-resistant bacteria is to modify and further develop antibiotic substances from commonly used classes like e.g. aminoglycosides, β-lactams, quinolones or macrolides:

Aminoglycosides have played a major role as efficious broad-spectrum antibiotics. Since the discovery of streptomycin, several other natural product-derived, semisynthetic aminoglycosides such as neomycin, kanamycin, paromomycin, gentamycin, tobramycin, sisomycin, amikacin, isepamacin, netilmicin and arbekacin have been developed (I. R. Hooper, *Aminoglycoside Antibiotics*, edited by H. Umezawa, I. R. Hooper, Springer Verlag, Berlin, 1982; P. Dozzo, H. E. Moser, *Expert Opin. Ther. Patents,* 2010, 20, 1321). Amikacin, for example, is often used for treating hospital-acquired infections with multidrug resistant Gram-negative bacteria such as *Enterobacter* and even *Pseudomonas aeruginosa* (E. M. Scholar, W. B. Pratt, *The Antimicrobial Drugs, 2$^{nd}$* edition, Oxford University Press, Inc. New York, 2000, 150). However, effective bacterial efflux pumps and/or enzymes that inactivate aminoglycosides by modifying the molecule by methylation, N-acetylation, 0-phosphorylation, or O-adenylation still constitute two major resistance mechanisms (P. Dozzo, H. E. Moser, *Expert Opin. Ther. Patents,* 2010, 20, 1321).

Since the wide therapeutic use of penicillin G, many improved β-lactam antibiotics have been designed and developed (K. Bush, M. J. Macielag, *Expert Opin. Ther. Patents,* 2010, 20, 1277). The β-lactam antibiotics comprise the penam (penicillin), penem, carbapenem, cephem (cephalosporins), carbacephem, and monobactam subfamilies. Ertapenem, a member of the carbapenem subfamily, is effective against Gram-positive and Gram-negative bacteria (L. L. Estes, J. W. Wilson, *Antimicrobials in Mayo Clinic*

*Internal Medicine Board Review*, edited by A. K. Gosh, Oxford University Press, Inc., 2010, 565) whereas penicillin G is noted to possess effectiveness mainly against Gram-positive organisms (L. L. Estes, J. W. Wilson, *Antimicrobials in Mayo Clinic Internal Medicine Board Review*, edited by A. K. Gosh, Oxford University Press, Inc., 2010, 560). An important mechanism of resistance to β-lactams is the hydrolysis of the β-lactam ring via β-lactamases. The emergence of various classes of β-lactamases has become a serious issue, especially in the fight against Gram-negative bacteria. Among the more recent β-lactam antibiotics being in late stage clinical development (Phase III) or marketed are the two anti-Methicillin-resistant *Staphylococcus aureus* (MRSA) cephalosporins ceftobiprole and ceftaroline (K. Bush, M. J. Macielag, *Expert Opin. Ther. Patents*, 2010, 20, 1277). However, they do not overcome resistance from Gram-negative bacteria producing extended spectrum β-lactamases (ESBLs) M. G. P. Page, *Curr. Opin. Pharmacol.*, 2006, 6, 480; K. M. Amsler, T. A. Davies, W. Shang et al., *Antimicrob. Agents Chemother.*, 2008, 52, 3418).

The quinolone class is one of the most important classes of antibiotics identified in the past 50 years. Due to their excellent broad-spectrum activity including Gram-negative pathogens the discovery of the fluoroquinolones as a second-generation quinolone antibiotics constituted a breakthrough in the 1980s. Ciprofloxacin, levofloxacin and moxifloxacin have become major pharmaceutical products whereupon ciprofloxacin remains the most potent quinolone against Gram-negative bacteria being effective against many susceptible strains of *Acinetobacter baumannii* and *Pseudomonas aeruginosa*, but quinolone resistance continues to increase (J. A. Wiles, B. J. Bradbury, M. J. Pucci, *Expert Opin. Ther. Patents*, 2010, 20, 1295).

One of the world's best-selling antibiotics, azithromycin, is an azalide being a subclass of the macrolide antibiotics. It has a similar spectrum as erythromycin and clarithromycin but is more effective against certain Gram-negative bacteria (L. L. Estes, J. W. Wilson, *Antimicrobials in Mayo Clinic Internal Medicine Board Review*, edited by A. K. Gosh, Oxford University Press, Inc., 2010, 568-569). However, *Pseudomonas aeruginosa* is considered to be resistant to azithromycin (T. Wagner, G. Soong, S. Sokol, L. Saiman, A. Prince, *Chest*, 2005, 128, 912).

As can be seen from the examples presented above the therapeutic use of even some of the most widespread broad-spectrum antibiotics is far from perfect, leaving loopholes for low responsive pathogens, such as e.g. *Pseudomonas aeruginosa*. Therefore the concept of using two or more, e.g. narrow and broad spectrum, antibiotic drugs in combination may lead to more efficacious and robust drugs having, for example, less incidences of bacterial resistance formation.

Historically different methodologies were employed to characterize the biological effect of two pharmaceutically active ingredients separate and in combination (E. Jawetz, *Antimicrob. Agents Chemother.*, 1967; 203-209; T.-C. Chou, P. Talalay, *Adv. Enzyme Regul.*, 1984, 22, 27-55). Meanwhile a broad consent is reached about the classification of observed drug-drug interaction, especially for antibiotics. According to this terminology the quantity of the combined dose-response effect of the drug-drug interaction is determined to be "additive" or "indifferent" if both active components behave independently of each other respectively have a similar joint action. The term "antagonism" is reserved for cases where a negative impact of the applied active compounds on each other can be seen, basically where they counteract each other. Finally "synergy" is used for cases where the dose-response is significantly potentiated above the intrinsic level of each individual drug alone (J. M. T. Hamilton-Miller, J. Antimicrob. Chemother., 1985, 15, 655-657; G. M. Eliopoulos, R. C. Moellering Jr., "*Antibiotics in laboratory medicine*", 1991, 3$^{rd}$ Ed., The William & Wilkins Co., 432-492).

The drug-drug interaction especially of antibiotics can be assessed at different clinical and preclinical stages. Currently the most widely used in vitro methods to study antibiotic combinations are the checkerboard technique leading to a fractional inhibitory concentration index and the killing curve method (H. O. Hallender et al., *Antimicrob. Agents Chemother.*, 1982; 22, 743-752; M. J. Hall et al., *J. Antimicrob. Chemother.*, 1983, 11, 427-433). Supplemented with a few techniques applying basically the same principles (e.g. R. C. Li et al., *Antimicrob. Agents Chemother.*, 1993; 37, 523-531; Chr. C. Sanders et al., *Antimicrob. Agents Chemother.*, 1993; 37, 260-264) the intention of these tests is primarily the identification of potential synergistic combinations for clinical application or to avoid the use of antagonistic combinations in clinical practice. However, all the in vitro techniques are hampered so far by the deficiency of standardization and especially of a lack of predictive power for the in vivo situation. Therefore in vivo experiments directly assessing the efficacy of the co-administered pharmaceutical compounds are strongly advised.

The present invention provides a novel combination comprising a β-hairpin peptidomimetic of the formula cyclo(-Thr-Trp-Ile-Dab-Orn-$^D$Dab-Dab-Trp-Dab-Dab-Ala-Ser-$^D$Pro-Pro)    (I), wherein
  Dab is (S)-2,4-diaminobutanoic acid;
  $^D$Dab is (R)-2,4-diaminobutanoic acid;
  Orn is (S)-2,5-diaminopentanoic acid;
all other amino acid residues are L-amino acid residues, if not explicitly designated as D-amino acid residues, following standard IUPAC nomenclature,
and
a further compound with antibiotic activity e.g. according to Ph. Eur. 7$^{th}$ (7.5) Edition,
or pharmaceutically acceptable salts, or hydrates or solvates thereof.

For avoidance of doubt, hereinafter follows a list of abbreviations, corresponding to generally adopted usual practice, of amino acids which, or the residues of which, are suitable for the purposes of the present invention and referred to in this document. The descriptors L respectively D, e.g. in $^D$Pro, refer to the stereochemistry at the α-position of the α-amino acid and are used according the Fischer-Rosanoff convention of the IUPAC.

| Ala | L-Alanine | (S)-2-aminopropanoic acid |
|---|---|---|
| Ile | L-Isoleucine | (2S,3S)-2-amino-3-methylpentanoic acid |
| Orn | L-Ornithine | (S)-2,5-diaminopentanoic acid |
| Pro | L-Proline | (S)-2-pyrrolidinecarboxylic acid |
| $^D$Pro | D-Proline | (R)-2-pyrrolidinecarboxylic acid |
| Ser | L-Serine | (S)-2-amino-3-hydroxypropanoic acid |
| Thr | L-Threonine | (2S,3R)-2-amino-3-hydroxybutanoic acid |
| Trp | L-Tryptophan | (S)-2-Amino-3-(1H-indol-3-yl)propanoic acid |
| Dab | | (S)-2,4-diaminobutanoic acid |
| $^D$Dab | | (R)-2,4-diaminobutanoic acid; |

In another embodiment this invention provides combinations of the β-hairpin peptidomimetic of formula (I) with an antibiotic compound selected from the classes of aminoglycosides, ansamycins, amphenicols, carbapenems, cephalosporins, diaminopyrimidines, glycopeptides, lincosamides, lipopeptides, macrolides, β-lactams, monobactams, nitrofurans, nitroimidazoles, oxazolidinones, penicillins, pleuromutilins, polypeptides, quinolones, rifamycins, streptogramins, sulfonamides, or tetracyclines, or pharmaceutically acceptable salts thereof.

In yet another embodiment of the invention the antibiotic compound in combination with the β-hairpin peptidomimetic of formula (I) is selected from ciprofloxacin, levofloxacin, moxifloxacin, gemifloxacin, ceftaroline, ceftobiprole, ceftazidime, ceftriaxone, cefepime, daptomycin, ramoplanin, vancomycin, colistin, polymyxin B, ertapenem, meropenem, doripenem, imipenem, aztreonam, piperacillin, amikacin, rifampicin, neomycin, gentamicin, tobramycin, fosfomycin, azithromycin, minocycline, doxycycline, or tetracycline, or a pharmaceutically acceptable salt thereof.

In a preferred embodiment this invention provides combinations of the β-hairpin peptidomimetic of formula (I) with an antibiotic compound selected from the classes of β-lactams, carbapenems, macrolides, quinolones, or aminoglycosides, or pharmaceutically acceptable salts thereof.

In another preferred embodiment of the invention the antibiotic compound in combination with the β-hairpin peptidomimetic of formula (I) is selected from ertapenem, azithromycin, ciprofloxacin, or amikacin, or a pharmaceutically acceptable salt thereof.

In an especially preferred embodiment this invention provides combinations of the β-hairpin peptidomimetic of formula (I) with an antibiotic compound selected from the class of carbapenems, or pharmaceutically acceptable salts thereof.

In another especially preferred embodiment this invention provides combinations of the β-hairpin peptidomimetic of formula (I) with an antibiotic compound selected from the class of macrolides, or pharmaceutically acceptable salts thereof.

In yet another especially preferred embodiment this invention provides combinations of the β-hairpin peptidomimetic of formula (I) with an antibiotic compound selected from the class of quinolones, or pharmaceutically acceptable salts thereof.

In still another especially preferred embodiment this invention provides combinations of the β-hairpin peptidomimetic of formula (I) with an antibiotic compound selected from the class of aminoglycosides, or pharmaceutically acceptable salts thereof.

In an especially preferred embodiment of the invention the antibiotic compound in combination with the β-hairpin peptidomimetic of formula (I) is ertapenem, or a pharmaceutically acceptable salt thereof.

In another especially preferred embodiment of the invention the antibiotic compound in combination with the β-hairpin peptidomimetic of formula (I) is azithromycin, or a pharmaceutically acceptable salt thereof.

In yet another especially preferred embodiment of the invention the antibiotic compound in combination with the β-hairpin peptidomimetic of formula (I) is ciprofloxacin, or a pharmaceutically acceptable salt thereof.

In still another especially preferred embodiment of the invention the antibiotic compound in combination with the β-hairpin peptidomimetic of formula (I) is amikacin, or a pharmaceutically acceptable salt thereof.

In another embodiment this invention provides a combination of compounds that enable therapeutic control of specific bacterial infections in human or animals at doses of the β-hairpin peptidomimetic of the formula (I) lower than the same compound administered alone.

Combinations comprising a β-hairpin peptidomimetic of formula (I) with a compound of the glycylcycline class, especially tigecycline, are subject of the applicants' co-pending application, filed simultaneously.

The combination of compounds of the invention can be used in a wide range of applications in order to inhibit the growth of or to kill microorganisms leading to the desired therapeutic effect in man or, due to their similar etiology, in other vertebrates. In particular the claimed combination can be used to inhibit the growth of or to kill microorganisms of a large panel of aerobic or anaerobic, Gram-positive or Gram-negative bacteria, or atypical organisms, but especially *Pseudomonas aeruginosa.*

When used to treat or prevent infections or diseases related to such infections, particularly nosocomial infections related to diseases such as ventilator-associated pneumonia (VAP), hospital-acquired pneumonia (HAP), healthcare-associated pneumonia (HCAP); catheter-related and non-catheter-related infections such as urinary tract infections (UTIs); related to respiratory diseases such as pneumonia, cystic fibrosis, emphysema and asthma; infections related to skin or soft tissue diseases such as surgical wounds, traumatic wounds and burn wounds; infections related to eye diseases such as keratitis and endophthalmitis; infections related to ear diseases such as otitis; infections related to CNS diseases such as brain abscess and meningitis; infections related to bone diseases such as osteochondritis and osteomyelitis; infections related to cardiovascular diseases such as endocarditis and pericarditis; blood stream infections (BSIs) such as septicemia; infections related to genitourinal diseases such as epididymitis, prostatitis and urethritis; infections related to gastrointestinal diseases such as epidemic diarrhea, necrotizing enterocolitis, typhlitis, gastroenteritis or pancreatitis; or intra-abdominal infections such as bacterial peritonitis; the compounds or respectively their pharmaceutical compositions as the components of the combination of the invention can be administered simultaneously as a single or separate physical entity as well as sequentially, i.e. with a certain time-shift according to dosage regime.

Therefore it is explicitly understood that these components act as a functional unity in a synergistic manner forming a specific embodiment of the invention as a "kit-of-parts".

In another specific embodiment of the invention the kit comprises a part containing a β-hairpin peptidomimetic of the formula (I), or a pharmaceutically acceptable salt thereof and a part containing a compound with antibiotic activity according to Ph. Eur. $7^{th}$ (7.5) Edition, or a pharmaceutically acceptable salt thereof.

In yet another specific embodiment of the invention the kit comprises a part containing a β-hairpin peptidomimetic of the formula (I), or a pharmaceutically acceptable salt thereof and a part containing an antibiotic compound selected from the classes of aminoglycosides, ansamycins, amphenicols, carbapenems, cephalosporins, diaminopyrimidines, glycopeptides, lincosamides, lipopeptides, macrolides, β-lactams, monobactams, nitrofurans, nitroimidazoles, oxazolidinones, penicillins, pleuromutilins, polypeptides, quinolones, rifamycins, streptogramins, sulfonamides, or tetracyclines, or pharmaceutically acceptable salts thereof.

In still another specific embodiment of the invention the kit comprises a part containing a β-hairpin peptidomimetic of the formula (I), or a pharmaceutically acceptable salt thereof and a part containing a compound with antibiotic activity selected from ertapenem, meropenem, azithromycin, ciprofloxacin, amikacin, neomycin, tobramycin, colistin, polymyxin B, minocycline, or tetracycline, or a pharmaceutically acceptable salt thereof.

In a preferred specific embodiment of the invention the kit comprises a part containing a β-hairpin peptidomimetic of the formula (I), or a pharmaceutically acceptable salt thereof and a part containing an antibiotic compound selected from the classes of β-lactams, carbapenems, macrolides, quinolones, or aminoglycosides, or pharmaceutically acceptable salts thereof.

In another preferred specific embodiment of the invention the kit comprises a part containing a β-hairpin peptidomimetic of the formula (I), or a pharmaceutically acceptable salt thereof and a part containing a compound with antibiotic activity selected from ertapenem, azithromycin, ciprofloxacin, or amikacin, or a pharmaceutically acceptable salt thereof.

In an especially preferred specific embodiment of the invention the kit comprises a part containing a β-hairpin peptidomimetic of the formula (I), or a pharmaceutically acceptable salt thereof and a part containing an antibiotic compound selected from the class of carbapenems, or pharmaceutically acceptable salts thereof.

In another especially preferred specific embodiment of the invention the kit comprises a part containing a β-hairpin peptidomimetic of the formula (I), or a pharmaceutically acceptable salt thereof and a part containing an antibiotic compound selected from the class of macrolides, or pharmaceutically acceptable salts thereof.

In yet another especially preferred specific embodiment of the invention the kit comprises a part containing a β-hairpin peptidomimetic of the formula (I), or a pharmaceutically acceptable salt thereof and a part containing an antibiotic compound selected from the class of quinolones, or pharmaceutically acceptable salts thereof.

In still another especially preferred specific embodiment of the invention the kit comprises a part containing a β-hairpin peptidomimetic of the formula (I), or a pharmaceutically acceptable salt thereof and a part containing an antibiotic compound selected from the class of aminoglycosides, or pharmaceutically acceptable salts thereof.

In an especially preferred specific embodiment of the invention the kit comprises a part containing a β-hairpin peptidomimetic of the formula (I), or a pharmaceutically acceptable salt thereof and a part containing ertapenem as a compound with antibiotic activity, or a pharmaceutically acceptable salt thereof.

In another especially preferred specific embodiment of the invention the kit comprises a part containing a β-hairpin peptidomimetic of the formula (I), or a pharmaceutically acceptable salt thereof and a part containing azithromycin as a compound with antibiotic activity, or a pharmaceutically acceptable salt thereof.

In yet another especially preferred specific embodiment of the invention the kit comprises a part containing a β-hairpin peptidomimetic of the formula (I), or a pharmaceutically acceptable salt thereof and a part containing ciprofloxacin as a compound with antibiotic activity, or a pharmaceutically acceptable salt thereof.

In still another especially preferred specific embodiment of the invention the kit comprises a part containing a β-hairpin peptidomimetic of the formula (I), or a pharmaceutically acceptable salt thereof and a part containing amikacin as a compound with antibiotic activity, or a pharmaceutically acceptable salt thereof.

Pharmaceutical compositions comprising the compounds of the invention, individually or in combination, may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active ingredients into preparations which can be used pharmaceutically. Proper formulation depends upon the method of administration chosen.

For topical administration the pharmaceutically active compounds of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the compounds of the invention may be formulated in adequate solutions, preferably in physiologically compatible buffers such as Hink's solution, Ringer's solution, or physiological saline buffer. The solution may contain formulatory agents such as suspending, stabilizing and/or dispersing agents. Alternatively, the active pharmaceutical ingredients of the invention may be in powder form for combination with a suitable vehicle, e.g. sterile pyrogen-free water, before use.

For transmucosal administration, penetrants appropriate to the barrier to be permeated are used in the formulation as known in the art.

For oral administration, the compounds of the invention can be readily formulated by combining with pharmaceutically acceptable carriers well-known in the art. Such carriers enable the compounds of the invention to be formulated as tablets, pills, dragees, capsules, liquids, gels, syrups, slurries, suspensions etc., for oral ingestion of a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, disintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added. For buccal administration, the composition may take the form of tablets, lozenges, etc. formulated as usual.

For administration by inhalation, the compounds of the invention can conveniently be delivered in form of an aerosol spray from pressurized packs or a nebulizer, with the use of a suitable propellant, e.g. dichlorodifluoromethane, trichlorofluoromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the compounds of the invention and a suitable powder base such as lactose or starch.

The compounds may also be formulated in rectal or vaginal compositions such as solutions for enema or suppositories together with appropriate suppository bases such as cocoa butter or other glycerides.

In addition to the formulations described previously, the compounds of the invention may also be formulated as depot preparations. Such long acting formulations may be administered by implantation (e.g. subcutaneously or intramuscularly) or by intramuscular injection. For the manufacture of such depot preparations the compounds of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well-known in the art. Certain organic solvents such as dimethylsulfoxide may also be employed. Additionally, the pharmaceutically active compounds of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 3 years. Depending on the chemical nature and the biological stability of the therapeutic agent, additional strategies for protein stabilization may be employed.

As the β-hairpin peptidomimetic as well as compounds of the other antibiotic classes of the invention may contain charged residues, respectively charged sub-structures, they may be, independently, included in any of the above-described formulations as such or as pharmaceutically acceptable salts. Pharmaceutically acceptable salts tend to be more soluble in aqueous and other protic solvents than are the corresponding free base forms.

In addition, the compounds of the present invention and their pharmaceutical acceptable salts may be used per se or in any appropriate formulation in morphological different solid state forms, which may or may not contain different amounts of solvent, e.g. hydrate remaining from the crystallization process.

The antibiotic combination of the invention, or compositions thereof, will generally be used in an amount and ratio effective to achieve the intended purpose. It is to be understood that the amount used will depend on a particular application.

For use to treat or prevent microbial infections or diseases related to such infections, the compounds of the invention, or compositions thereof, are administered or applied in a therapeutically effective amount. By therapeutically effective amount is meant an amount effective in ameliorating the symptoms of, or in ameliorating, treating or preventing microbial infections or diseases related thereto. Determination of a therapeutically effective amount is well within the capacities of those skilled in the art.

For systemic administration, a therapeutically effective dose can be estimated initially from in vitro assays. For example, a dose can be formulated in animal models to achieve a circulating active pharmaceutical ingredient concentration range that includes the $IC_{50}$ as determined in the cell culture (i.e. the concentration of a test compound that is lethal to 50% of a cell culture), the MIC, as determined in cell culture (i.e. the concentration of a test compound that prevents visible growth of a microorganism). Initial dosages can also be determined from in vivo data, e.g. animal models, using techniques that are well known in the art, e.g. as described below in the example part. One having ordinary skills in the art could readily optimize administration to humans based on animal data.

The effective dosage of the active ingredients employed may vary depending on the particular compound or pharmaceutical preparation employed, the mode of administration and the severity and type of the condition treated. Thus, the dosage regimen is selected in accordance with factors including the route of administration and the clearance pathway, e.g. the renal and hepatic function of the patient. A physician, clinician or veterinarian skilled in the art can readily determine and prescribe the amount of the single active ingredient or combination thereof required to prevent, ameliorate or arrest the progress of the condition or disease. Optimal precision in achieving concentration of active ingredients without toxicity requires a regimen based on the kinetics of the active ingredients' availability to the target sites. This involves a consideration of the distribution, equilibrium, and elimination of the active ingredients.

In cases of local administration or selective uptake, the effective local concentration of the compounds of the invention may not be related to plasma concentration. One having the skills in the art will be able to optimize therapeutically effective local dosages without undue experimentation.

Further parameters determining the efficacy, dose, dose regimen and general therapeutic index as a medicament in a clinical setting for the combination or as well for the individual compounds of the invention can be pre-assessed by various in vitro assays. Some of these key parameters are e.g. the minimal bactericidal concentration, minimal inhibitory concentration, antibacterial killing curves, cytotoxicity, hemolysis, plasma stability respectively plasma half-life, microsomal stability, drug metabolism (including drug-drug interaction), protein binding, membrane permeability, solubility etc.

The invention will now be further described in the Examples below, which are intended as an illustration only and not to be construed as limiting the scope of the invention in any way.

EXAMPLES

In Vivo Efficacy Test:
Efficacy in Murine Pneumonia Model Against *Pseudomonas aeruginosa* PAX11045 and Estimation of $ED_{50}$
Reference 1:
The efficacy and $ED_{50}$ of the compound of formula (I) ("compound 1") was determined against *Pseudomonas aeruginosa* clinical isolate PAX11045 in a pneumonia model in mice. Colony counts in the lungs and spleen were determined at 20 hours post treatment.

Infection of Mice
Fresh overnight colonies of PAX11045 from a 5% Horse Blood Agar plate were suspended in 0.9% sterile saline to approximately $10^8$ CFU/ml and further diluted to approximately $5 \times 10^7$ CFU/ml. Female mice (DBA/2, outbred, 18-22 g, Charles River) were anesthetized with 0.08 ml of Zoletil (tiletamine+zolazepam) and inoculated via the nose with a pipette with 0.05 ml of the bacteria suspension containing approximately $10^6$ CFU. 4 hours after inoculation, the mice were treated orally with 45 µl neurophen (20 mg ibuprofen/ml corresponding to approximately 30 mg/kg) as pain relief.

Treatment of Mice with Compound 1
Two vials containing 10 mg of active compound 1 were dissolved in 2.25 ml 0.9% sterile saline each to a concentration of 4.5 mg/ml. One vial was further 2-fold diluted with saline to 2.25, 1.125, 0.56 and 0.28 mg/ml. The mice were treated subcutaneously with 0.2 ml in the neck region with a single dose at 4 hours post infection with a dose calculation based on a mean animal weight of 20 g. As positive control ciprofloxacin was used in the same manner with a fixed dose of 19 mg/kg.

Sampling

Colony counts were determined post inoculation at 4 hours (untreated mice) and 24 hours (treated and vehicle-only treated mice). Immediately after the mice were sacrificed, the lungs and spleens were collected and frozen at −20° C. After thawing, the organs were homogenized in 1 ml 0.9% saline. Each sample was then 10-fold diluted in saline and 20 µl spots were applied on blood agar plates. All agar plates were incubated 18-48 hours at 35° C. in ambient air.

CFU Counts

The CFU/ml in the inoculum was determined to 7.92 $\log_{10}$ CFU/ml corresponding to 6.62 $\log_{10}$ CFU/mouse.

At 4 hours after infection the mean $\log_{10}$ CFU/lung was 5.28 and the CFU level remained at a similar level after 24 hours in the vehicle-only group. Analog baseline data were collected for the spleen with a mean $\log_{10}$ CFU/spleen of 1.96 at 4 hours, which increased to 2.60 after 24 hours in the vehicle-only group.

Treatment with compound 1 resulted in both organs in a concentration dependent significant reduction of the CFU levels compared to vehicle treatment ($p<0.001$ for the higher concentrations). Also ciprofloxacin (19 mg/kg) had a significant effect on reducing the bacterial loads ($p<0.001$).

Evaluation of the dose-response curve for $ED_{50}$ of compound 1 against PAX11045 in murine lungs using a sigmoidal dose-response model (variable slope) revealed an estimation of 4.33 mg/kg. Table 1 below summarizes the relevant efficacy values.

Example 1

The efficacy and $ED_{50}$ of the compound of formula (I) ("compound 1") in combination with ertapenem was determined against *Pseudomonas aeruginosa* clinical isolate PAX11045 in a pneumonia model in mice. Colony counts in lung were determined at 20 hours post treatment.

Infection of Mice

Fresh overnight colonies of PAX11045 from a 5% Horse Blood Agar plate were suspended in 0.9% sterile saline to approximately $10^8$ CFU/ml and further diluted to approximately $5\times10^7$ CFU/ml. Female mice (DBA/2, outbred, 18-22 g, Charles River) were anesthetized with 0.1 ml of Zoletil and inoculated via the nose with a pipette with 0.05 ml of the bacteria suspension containing approximately $10^6$ CFU. 4 hours after inoculation, the mice were treated orally with 45 µl neurophen (20 mg ibuprofen/ml corresponding to approximately 30 mg/kg) as pain relief.

Treatment of Mice with Ertapenem 1 g of ertapenem (Invanz™, MSD Denmark Aps) was dissolved in 10 ml 0.9% sterile saline to a concentration of 100 mg/ml and further diluted with saline to 5 mg/ml. The mice were treated subcutaneously with 0.2 ml in the neck region with a single dose at 3 hours post infection corresponding to 50 mg/kg on the basis of a mean animal weight of 20 g.

Treatment of Mice with Compound 1

One vial containing 10 mg of active compound 1 was dissolved in 2 ml 0.9% sterile saline to a concentration of 5 mg/ml and further diluted with saline to 2, 1, 0.55, 0.275 and 0.137 mg/ml. The mice were treated subcutaneously with 0.2 ml in the neck region with a single dose at 4 hours post infection with a dose calculation based on a mean animal weight of 20 g. As positive control ciprofloxacin was used in the same manner with a fixed dose of 20 mg/kg.

Sampling

Colony counts were determined post inoculation at 4 hours (untreated mice) and 24 hours (treated and vehicle-only treated mice). Immediately after the mice were sacrificed, the lungs were collected and frozen at −20° C. After thawing, the organs were homogenized in 1 ml 0.9% saline. Each sample was then 10 fold diluted in saline and 20 µl spots were applied on blood agar plates. All agar plates were incubated 18-24 hours at 35° C. in ambient air.

CFU Counts

The CFU/ml in the inoculum was determined to 7.65 $\log_{10}$ CFU/ml corresponding to 6.35 $\log_{10}$ CFU/mouse.

At 4 hours after infection the mean $\log_{10}$ CFU/lung was 5.14 and the CFU level remained at a similar level after 24 hours in the vehicle-only group.

Treatment with a combination of compound 1 and ertapenem resulted in a concentration dependent significant reduction of the CFU levels compared to vehicle treatment ($p<0.01$-$p<0.001$). Also ciprofloxacin treatment (20 mg/kg), compound 1 (2.75 mg/kg) alone and ertapenem (50 mg/kg) alone had a significant effect on reducing the bacterial loads ($p<0.001$).

Evaluation of the dose-response curve for $ED_{50}$ of compound 1 in presence of a fixed dose of ertapenem (50 mg/kg) against PAX11045 in murine lungs using a sigmoidal dose-response model (variable slope) revealed an estimation of 1.24 mg/kg. Table 1 below summarizes the relevant efficacy values.

TABLE 1

Efficacy values of compound 1

| | compound 1 | compound 1 in presence of 50 mg/kg ertapenem |
|---|---|---|
| Top level | 1.3 $\log_{10}$ CFU/ml | −0.34 $\log_{10}$ CFU/ml |
| Bottom level | −2.2 $\log_{10}$ CFU/ml | −2.32 $\log_{10}$ CFU/ml |
| $E_{max}$ | 3.5 $\log_{10}$ CFU/ml | 1.98 $\log_{10}$ CFU/ml |
| $ED_{50}$ | 4.33 mg/kg | 1.24 mg/kg |
| Static dose | 1.55 mg/kg | 0.63 mg/kg |
| 1 log killing dose | 8.1 mg/kg | 1.14 mg/kg |
| 2 log killing dose | 20 mg/kg | 1.48 mg/kg |
| $R^2$ | 0.55-0.75 | 0.54 |

Example 2

The efficacy and $ED_{50}$ of the compound of formula (I) ("compound 1") in combination with azithromycin was determined against *Pseudomonas aeruginosa* clinical isolate PAX11045 in a pneumonia model in mice. Colony counts in lung were determined at 20 hours post treatment.

Infection of Mice

Fresh overnight colonies of PAX11045 from a 5% Horse Blood Agar plate were suspended in 0.9% sterile saline to approximately $10^8$ CFU/ml and further diluted to approximately $5\times10^7$ CFU/ml. Female mice (DBA/2, outbred, 17-23 g, Charles River) were anesthetized with 0.1 ml of Zoletil and inoculated via the nose with a pipette with 0.05 ml of the bacteria suspension containing approximately $10^6$ CFU. 4 hours after inoculation, the mice were treated orally with 45 µl neurophen (20 mg ibuprofen/ml corresponding to approximately 30 mg/kg) as pain relief.

Treatment of Mice with Azithromycin 480 mg of azithromycin (Zitromax™, Pfizer) were dissolved in 4.8 ml 0.9% sterile saline to a concentration of 100 mg/ml and further diluted with saline to 5 mg/ml. The mice were treated subcutaneously with 0.2 ml in the neck region with a single dose at 3 hours post infection corresponding to 50 mg/kg on the basis of a mean animal weight of 20 g.

Treatment of Mice with Compound 1

One vial containing 10 mg of active compound 1 was dissolved in 2 ml 0.9% sterile saline to a concentration of 5 mg/ml and further diluted with saline to 2, 1, 0.55, 0.275 and 0.137 mg/ml. The mice were treated subcutaneously with 0.2 ml in the neck region with a single dose at 4 hours post infection with a dose calculation based on a mean animal weight of 20 g. As positive control ciprofloxacin was used in the same manner with a fixed dose of 20 mg/kg.

Sampling

Colony counts were determined post inoculation at 4 hours (untreated mice) and 24 hours (treated and vehicle-only treated mice). Immediately after the mice were sacrificed, the lungs were collected and frozen at −20° C. After thawing, the organs were homogenized in 1 ml 0.9% saline. Each sample was then 10 fold diluted in saline and 20 μl spots were applied on blood agar plates. All agar plates were incubated 18-24 hours at 35° C. in ambient air.

CFU Counts

The CFU/ml in the inoculum was determined to 7.3 $\log_{10}$ CFU/ml corresponding to 6.0 $\log_{10}$ CFU/mouse.

At 4 hours after infection the mean $\log_{10}$ CFU/lung was 5.84 and the CFU level remained at a similar level after 24 hours in the vehicle-only group.

Treatment with a combination of compound 1 and azithromycin resulted in a concentration dependent significant reduction of the CFU levels compared to vehicle treatment ($p<0.01$-$p<0.001$). Also ciprofloxacin treatment (20 mg/kg) and treatment with compound 1 (5.5 mg/kg) alone had a significant effect on reducing the bacterial loads ($p<0.001$). Treatment with azithromycin (50 mg/kg) alone had no effect on the bacterial loads.

Evaluation of the dose-response curve for $ED_{50}$ of compound 1 in presence of a fixed dose of azithromycin (50 mg/kg) against PAX11045 in murine lungs using a sigmoidal dose-response model (variable slope) revealed an estimation of 1.74 mg/kg. Table 2 below summarizes the relevant efficacy values.

TABLE 2

Efficacy values of compound 1

|  | compound 1 | compound 1 in presence of 50 mg/kg azithromycin |
|---|---|---|
| Top level | 1.3 $\log_{10}$ CFU/ml | −0.10 $\log_{10}$ CFU/ml |
| Bottom level | −2.2 $\log_{10}$ CFU/ml | −2.59 $\log_{10}$ CFU/ml |
| $E_{max}$ | 3.5 $\log_{10}$ CFU/ml | 2.49 $\log_{10}$ CFU/ml |
| $ED_{50}$ | 4.33 mg/kg | 1.74 mg/kg |
| Static dose | 1.55 mg/kg | 0.63 mg/kg |
| 1 log killing dose | 8.1 mg/kg | 1.2 mg/kg |
| 2 log killing dose | 20 mg/kg | 2.4 mg/kg |
| $R^2$ | 0.55-0.75 | 0.52 |

Efficacy in Murine Pneumonia Model Against *Pseudomonas aeruginosa* PA9349 and Estimation of $ED_{50}$ Reference 2:

The efficacy and $ED_{50}$ of the compound of formula (I) ("compound 1") was determined against *Pseudomonas aeruginosa* clinical isolate PA9349 in a pneumonia model in mice. Colony counts in the lungs were determined at 18-20 hours post treatment.

Infection of Mice

Fresh overnight colonies of PA9349 from a 5% Horse Blood Agar plate were suspended in 0.9% sterile saline to approximately $10^8$ CFU/ml and further diluted to approximately $5\times10^6$ CFU/ml. Female mice (DBA/2, outbred, 18-22 g, Charles River) were anesthetized with 0.1 ml of Zoletil (tiletamine+zolazepam) and inoculated via the nose with a pipette with 0.05 ml of the bacteria suspension containing approximately $5\times10^5$ CFU. 4 hours after inoculation, the mice were treated orally with 45 μl neurophen (20 mg ibuprofen/ml corresponding to approximately 30 mg/kg) as pain relief.

Treatment of Mice with Compound 1

One vial containing 10 mg of active compound 1 was dissolved in 5 ml 0.9% sterile saline to a concentration of 2 mg/ml and was further 2-fold diluted with saline to 1, 0.5, 0.25, 0.125 and 0.06 mg/ml. The mice were treated subcutaneously with 0.2 ml in the neck region with a single dose at 4 hours post infection with a dose calculation based on a mean animal weight of 20 g. As positive control colistin was used in the same manner with a fixed dose of 40 mg/kg.

Sampling

Colony counts were determined post inoculation at 4 hours (untreated mice) and 24 hours (treated and vehicle-only treated mice). Immediately after the mice were sacrificed, the lungs were collected and frozen at −20° C. After thawing, the organs were homogenized in 1 ml 0.9% saline. Each sample was then 10-fold diluted in saline and 20 μl spots were applied on blood agar plates. All agar plates were incubated 18-48 hours at 35° C. in ambient air.

CFU Counts

The CFU/ml in the inoculum was determined to 7.29 $\log_{10}$ CFU/ml corresponding to 5.98 $\log_{10}$ CFU/mouse.

At 4 hours after infection the mean $\log_{10}$ CFU/lung was 3.47 and the CFU level increased to 4.92 at 20 hours post inoculation in the vehicle-only group.

A reduction of the mean CFU level compared to the vehicle group was observed in the 10 mg/kg compound 1 treatment group whereupon a significant reduction was observed in the 20 mg/kg compound 1 treatment group.

Evaluation of the dose-response curve for $ED_{50}$ of compound 1 against PA9349 in murine lungs using a sigmoidal dose-response model (variable slope) revealed an estimation of 7.35 mg/kg. Table 3 below summarizes the relevant efficacy values.

Example 3

The efficacy and $ED_{50}$ of the compound of formula (I) ("compound 1") in combination with ciprofloxacin was determined against *Pseudomonas aeruginosa* clinical isolate PA9349 in a pneumonia model in mice. Colony counts in lung were determined at 20 hours post treatment.

Infection of Mice

Fresh overnight colonies of PA9349 from a 5% Horse Blood Agar plate were suspended in 0.9% sterile saline to approximately $10^8$ CFU/ml and further diluted to approximately $10^7$ CFU/ml. Female mice (C57BL/6 male, outbred, 20-25 g, Hellenic Pasteur Institute) were anesthetized with ether and inoculated via the nose with a pipette with 0.05 ml of the bacteria suspension containing approximately $10^6$ CFU. After inoculation, mice were treated with paracetamol suppositories as a pain relief.

Treatment of Mice with Ciprofloxacin 400 mg of ciprofloxacin (Sigma) was dissolved in 0.9% sterile saline to a concentration of 10 mg/ml and further diluted with saline to 2 mg/ml. The mice were treated subcutaneously with 0.2 ml in the neck region with a single dose at 3 hours post infection corresponding to 20 mg/kg on the basis of a mean animal weight of 20 g.

Treatment of Mice with Compound 1

One vial containing 5 mg of active compound 1 was dissolved in 2.5 ml 0.9% sterile saline to a concentration of 2 mg/ml. 1 vial was further diluted with saline to 1, 0.8 and 0.4 mg/ml. The mice were treated subcutaneously with 0.25 ml (25 mg/kg dose) or 0.2 ml (for all other doses) in the neck region with a single dose at 4 hours post infection with a dose calculation based on a mean animal weight of 20 g. As controls colistin and ciprofloxacin were used in the same manner with a fixed dose of 20 mg/kg.

Sampling

Colony counts were determined post inoculation at 4 hours (untreated mice) and 24 hours (treated and vehicle-only treated mice). Immediately after the mice were sacrificed, the lungs were collected and frozen at −20° C. After thawing, the organs were homogenized in 1 ml 0.9% saline. Each sample was then 10 fold diluted in saline and 20 µl spots were applied on blood agar plates. All agar plates were incubated 18-24 hours at 35° C. in ambient air.

CFU Counts

The CFU/ml in the inoculum was determined to 7.0 $\log_{10}$ CFU/ml corresponding to 5.8 $\log_{10}$ CFU/mouse.

At 4 hours after infection the mean $\log_{10}$ CFU/lung was 5.63 and the CFU level remained at a similar level after 24 hours in the vehicle-only group.

Treatment with a combination of compound 1 at 1.88-25 mg/kg and ciprofloxacin resulted in a significant reduction of the CFU levels compared to vehicle treatment (p<0.001). Treatment with compound 1 (5.5 mg/kg) alone had a significant effect on reducing the bacterial loads (p<0.001) whereupon colistin treatment (20 mg/kg) alone and ciprofloxacin treatment (20 mg/kg) alone had no or only slight effects on the bacterial loads.

Evaluation of the dose-response curve for $ED_{50}$ of compound 1 in presence of a fixed dose of ciprofloxacin (20 mg/kg) against PA9349 in murine lungs using a sigmoidal dose-response model (variable slope) revealed an estimation of 1.55 mg/kg. Table 3 below summarizes the relevant efficacy values.

TABLE 3

Efficacy values of compound 1

|  | compound 1 | compound 1 in presence of 20 mg/kg ciprofloxacin |
| --- | --- | --- |
| Top level | 1.59 $\log_{10}$ CFU/ml | −0.21 $\log_{10}$ CFU/ml |
| Bottom level | −0.80 $\log_{10}$ CFU/ml | −4.17 $\log_{10}$ CFU/ml |
| $E_{max}$ | −2.4 $\log_{10}$ CFU/ml | 3.96 $\log_{10}$ CFU/ml |
| $ED_{50}$ | 7.35 mg/kg | 1.55 mg/kg |
| Static dose | 9.15 mg/kg | nd |
| 1 log killing dose | nd | 0.45 mg/kg |
| 2 log killing dose | nd | 1.00 mg/kg |
| 3log killing dose | nd | 1.82 mg/kg |
| $R^2$ | 0.67 | 0.54 | nd: not determined

Efficacy in Murine Pneumonia Model Against *Pseudomonas aeruginosa* PA18298 and Estimation of $ED_{50}$ Reference 3:

The efficacy and $ED_{50}$ of the compound of formula (I) ("compound 1") was determined against *Pseudomonas aeruginosa* clinical isolate PA18298 in a pneumonia model in mice. Colony counts in the lungs were determined at 18-20 hours post treatment.

Infection of Mice

Fresh overnight colonies of PA18298 from a 5% Horse Blood Agar plate were suspended in 0.9% sterile saline to approximately $10^8$ CFU/ml and further diluted to approximately $4\times10^7$ CFU/ml. Female mice (DBA/2, outbred, 18-22 g, Charles River) were anesthetized with 0.1 ml of Zoletil (tiletamine+zolazepam) and inoculated via the nose with a pipette with 0.05 ml of the bacteria suspension containing approximately $1\times10^6$ CFU. 4 hours after inoculation, the mice were treated orally with 45 µl neurophen (20 mg ibuprofen/ml corresponding to approximately 30 mg/kg) as pain relief.

Treatment of Mice with Compound 1

One vial containing 10 mg of active compound 1 was dissolved in 2 ml 0.9% sterile saline to a concentration of 5 mg/ml and was further diluted with saline to 2, 1, 0.75, 0.55, 0.275 and 0.137 mg/ml. The mice were treated subcutaneously with 0.2 ml in the neck region with a single dose at 4 hours post infection with a dose calculation based on a mean animal weight of 20 g. As positive control colistin was used in the same manner with a fixed dose of 20 mg/kg.

Sampling

Colony counts were determined post inoculation at 4 hours (untreated mice) and 24 hours (treated and vehicle-only treated mice). Immediately after the mice were sacrificed, the lungs were collected and frozen at −20° C. After thawing, the organs were homogenized in 1 ml 0.9% saline. Each sample was then 10-fold diluted in saline and 20 µl spots were applied on blood agar plates. All agar plates were incubated 18-48 hours at 35° C. in ambient air.

CFU Counts

The CFU/ml in the inoculum was determined to 7.49 $\log_{10}$ CFU/ml corresponding to 6.20 $\log_{10}$ CFU/mouse.

At 4 hours after infection the mean $\log_{10}$ CFU/lung was 5.05 and the CFU level declined to 2.62 at 24 hours post inoculation in the vehicle-only group.

Treatment with POL7080 at 11-20 mg/kg resulted in significant reduction of the CFU levels compared to vehicle treatment (p<0.01-p<0.001). Also colistin treatment (20 mg/kg) had some effect on reducing the bacterial loads (p<0.001).

Evaluation of the dose-response curve for $ED_{50}$ of compound 1 against PA18298 in murine lungs using a sigmoidal dose-response model (variable slope) revealed an estimation of 26.6 mg/kg. Table 4 below summarizes the relevant efficacy values.

Example 4

The efficacy and $ED_{50}$ of the compound of formula (I) ("compound 1") in combination with amikacin was determined against *Pseudomonas aeruginosa* clinical isolate PA18298 in a pneumonia model in mice. Colony counts in lung were determined at 20 hours post treatment.

Infection of Mice

Fresh overnight colonies of PA18298 from a 5% Horse Blood Agar plate were suspended in 0.9% sterile saline to approximately $10^8$ CFU/ml and further diluted to approximately $5\times10^7$ CFU/ml. Female mice (DBA/2, outbred, 18-22 g, Charles River) were anesthetized with 0.1 ml of Zoletil and inoculated via the nose with a pipette with 0.05 ml of the bacteria suspension containing approximately $10^6$ CFU. 4 hours after inoculation, the mice were treated orally with 45 µl neurophen (20 mg ibuprofen/ml corresponding to approximately 30 mg/kg) as pain relief.

Treatment of Mice with Amikacin 175 mg of amikacin (Sigma) were dissolved in 5 ml 0.9% sterile saline to a concentration of 35 mg/ml and further diluted with saline to 3 mg/ml. The mice were treated subcutaneously with 0.2 ml in the neck region with a single dose at 3 hours post infection corresponding to 30 mg/kg on the basis of a mean animal weight of 20 g.

Treatment of Mice with Compound 1

One vial containing 10 mg of active compound 1 was dissolved in 2 ml 0.9% sterile saline to a concentration of 5 mg/ml and further diluted with saline tot, 1, 0.55, 0.275 and 0.137 mg/ml. The mice were treated subcutaneously with 0.2 ml in the neck region with a single dose at 4 hours post infection with a dose calculation based on a mean animal weight of 20 g. Colistin was used as a control in the same manner with a fixed dose of 20 mg/kg.

Sampling

Colony counts were determined post inoculation at 4 hours (untreated mice) and 24 hours (treated and vehicle-only treated mice). Immediately after the mice were sacrificed, the lungs were collected and frozen at −20° C. After thawing, the organs were homogenized in 1 ml 0.9% saline. Each sample was then 10 fold diluted in saline and 20 μl spots were applied on blood agar plates. All agar plates were incubated 18-24 hours at 35° C. in ambient air.

CFU Counts

The CFU/ml in the inoculum was determined to 7.4 $\log_{10}$ CFU/ml corresponding to 6.17 $\log_{10}$ CFU/mouse.

mg/kg) alone had some effects on reducing the bacterial loads.

Evaluation of the dose-response curve for $ED_{50}$ of compound 1 in presence of a fixed dose of amikacin (30 mg/kg) against PA18298 in murine lungs using a sigmoidal dose-response model (variable slope) revealed an estimation of 9.1 mg/kg. Table 4 below summarizes the relevant efficacy values.

TABLE 4

Efficacy values of compound 1

|  | compound 1 | compound 1 in presence of 30 mg/kg amikacin |
| --- | --- | --- |
| Top level | −3.60 $\log_{10}$ CFU/ml | −3.03 $\log_{10}$ CFU/ml |
| Bottom level | −2.48 $\log_{10}$ CFU/ml | −3.82 $\log_{10}$ CFU/ml |
| $E_{max}$ | 1.12 $\log_{10}$ CFU/ml | 0.79 $\log_{10}$ CFU/ml |
| $ED_{50}$ | 26.6 mg/kg | 9.1 mg/kg |
| Static dose | 9.15 mg/kg | nd |
| 1 log killing dose | nd | nd |
| 2 log killing dose | nd | nd |
| $R^2$ | 0.26 | 0.05 | nd: not determined

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (4)..(4)
<223> OTHER INFORMATION: Dab
<220> FEATURE:
<221> NAME/KEY: MISC_FEATURE
<222> LOCATION: (5)..(5)
<223> OTHER INFORMATION: Orn
<220> FEATURE:
<221> NAME/KEY: MISC_FEATURE
<222> LOCATION: (6)..(6)
<223> OTHER INFORMATION: DDab
<220> FEATURE:
<221> NAME/KEY: MISC_FEATURE
<222> LOCATION: (7)..(7)
<223> OTHER INFORMATION: Dab
<220> FEATURE:
<221> NAME/KEY: MISC_FEATURE
<222> LOCATION: (9)..(9)
<223> OTHER INFORMATION: Dab
<220> FEATURE:
<221> NAME/KEY: MISC_FEATURE
<222> LOCATION: (10)..(10)
<223> OTHER INFORMATION: Dab
<220> FEATURE:
<221> NAME/KEY: MISC_FEATURE
<222> LOCATION: (13)..(13)
<223> OTHER INFORMATION: DPro

<400> SEQUENCE: 1

Thr Trp Ile Xaa Xaa Xaa Xaa Trp Xaa Xaa Ala Ser Xaa Pro
1               5                   10
```

At 4 hours after inoculation the mean log 10 CFU/lung was 5.06 and the CFU level declined to 1.55 mean log 10 CFU/lung after 24 hours in the vehicle group. Colistin treatment (20 mg/kg) as well as amikacin treatment (30

The invention claimed is:

1. A combination comprising a β-hairpin peptidomimetic of the formula cyclo(-Thr-Trp-Ile-Dab-Orn-$^D$Dab-Dab-Trp-Dab-Dab-Ala-Ser-$^D$Pro-Pro) (I), wherein
Dab is (S)-2,4-diaminobutanoic acid;
$^D$Dab is (R)-2,4-diaminobutanoic acid;
Orn is (S)-2,5-diaminopentanoic acid;
and
a further antibiotic compound selected from ciprofloxacin, levofloxacin, moxifloxacin, gemifloxacin, ceftaroline, ceftobiprole, ceftazidime, ceftriaxone, cefepime, daptomycin, ramoplanin, vancomycin, colistin, polymyxin B, ertapenem, meropenem, doripenem, imipenem, aztreonam, piperacillin, amikacin, rifampicin, neomycin, gentamicin, tobramycin, fosfomycin, azithromycin, minocycline, doxycycline, or tetracycline,
or a pharmaceutically acceptable salt thereof.

2. The combination according to claim 1 wherein the further antibiotic compound is selected from ertapenem, azithromycin, ciprofloxacin, or amikacin, or a pharma-ceutically acceptable salt thereof.

3. The combination according to claim 1 wherein the further antibiotic compound is selected from the class of macrolides, or pharmaceutically acceptable salts thereof.

4. The combination according to claim 1 wherein the further antibiotic compound is selected from the class of quinolones, or pharmaceutically acceptable salts thereof.

5. The combination according to claim 1 wherein the further antibiotic compound is selected from the class of aminoglycosides, or pharmaceutically acceptable salts thereof.

6. The combination according to claim 1 wherein the further antibiotic compound is ertapenem, or a pharmaceutically acceptable salt thereof.

7. The combination according to claim 1 wherein the further antibiotic compound is azithromycin, or a pharmaceutically acceptable salt thereof.

8. The combination according to claim 1 wherein the further antibiotic compound is ciprofloxacin, or a pharmaceutically acceptable salt thereof.

9. The combination according to claim 1 wherein the further antibiotic compound is amikacin, or a pharmaceutically acceptable salt thereof.

10. The combination according to claim 1 for use in medicine.

11. The combination according to claim 1 for the treatment of bacterial infections or diseases related to such infections in human or animals.

12. A method for manufacturing a pharmaceutical compositing comprising the combination according to claim 1, comprising:
formulating the pharmaceutical composition for the treatment of bacterial infections or diseases related to such infections in human or animals.

13. A pharmaceutical composition containing a combination according to claim 1 and at least one pharmaceutically inert carrier.

14. The pharmaceutical composition according to claim 13 in a form suitable for oral, topical, transdermal, injection, infusion, buccal, transmucosal, rectal, vaginal, pulmonary or inhalation administration, especially in the form of tablets, dragees, capsules, solutions, liquids, gels, plaster, creams, ointments, syrup, slurries, powders, suspensions, spray, nebulizer or suppositories.

15. A method for the treatment of bacterial infections or diseases related to such infections in a human or an animal, comprising:
administering a therapeutically effective amount of the pharmaceutical composition according to claim 13 to the human or the animal.

16. A kit comprising a part containing a β-hairpin peptidomimetic of the formula (I) according to claim 1, or a pharmaceutically acceptable salt thereof.

17. A kit comprising a part containing a β-hairpin peptidomimetic of the formula (I) according to claim 1, or a pharmaceutically acceptable salt thereof and a part containing a compound with antibiotic activity selected from the classes of β-lactams, carbapenems, macrolides, quinolones, or aminoglycosides, or pharmaceutically acceptable salts thereof.

18. A kit according to claim 16 wherein the compound with antibiotic activity is selected from ertapenem, meropenem, azithromycin, ciprofloxacin, amikacin, neomycin, tobramycin, colistin, polymyxin B, minocycline, or tetracycline,
or a pharmaceutically acceptable salt thereof.

19. A kit according to claim 16 wherein the compound with antibiotic activity is selected from ertapenem, azithromycin, ciprofloxacin, or amikacin, or a pharmaceutically acceptable salt thereof.

20. A kit according to claim 16 wherein the compound with antibiotic activity is ertapenem, or a pharmaceutically acceptable salt thereof.

21. A kit according to claim 16 wherein the compound with antibiotic activity is azithromycin, or a pharmaceutically acceptable salt thereof.

22. A kit according to claim 16 wherein the compound with antibiotic activity is ciprofloxacin, or a pharmaceutically acceptable salt thereof.

23. A kit according to claim 16 wherein the compound with antibiotic activity is amikacin$^{AG}$, or a pharmaceutically acceptable salt thereof.

24. A method of treating an bacterial infection or disease related to such infection in human or animals comprising administering to a subject in need thereof an adequate amount of a combination according to claim 1.

* * * * *